(12) United States Patent
Saxena et al.

(10) Patent No.: US 8,701,494 B1
(45) Date of Patent: Apr. 22, 2014

(54) APPARATUS AND METHOD FOR DAMAGE LOCATION AND IDENTIFICATION IN STRUCTURES

(75) Inventors: Indu Saxena, Torrance, CA (US); Lothar Kempen, Redondo Beach, CA (US); Chai Tea, El Monte, CA (US)

(73) Assignee: Optech Ventures, LLC, Torrance, CA (US)

( * ) Notice: Subject to any disclaimer, the term of this patent is extended or adjusted under 35 U.S.C. 154(b) by 0 days.

(21) Appl. No.: 13/569,049

(22) Filed: Aug. 7, 2012

Related U.S. Application Data

(63) Continuation of application No. 12/504,595, filed on Jul. 16, 2009, now Pat. No. 8,234,924.

(60) Provisional application No. 61/081,706, filed on Jul. 17, 2008.

(51) Int. Cl.
*G01N 29/00* (2006.01)
*G02B 6/00* (2006.01)

(52) U.S. Cl.
USPC ............ 73/632; 73/655; 73/657; 385/13

(58) Field of Classification Search
USPC ............ 73/632, 655, 657; 385/7, 13, 89; 359/305–314, 285–287
See application file for complete search history.

(56) References Cited

U.S. PATENT DOCUMENTS

| | | | | |
|---|---|---|---|---|
| 5,502,782 A * | 3/1996 | Smith | | 385/7 |
| 6,411,748 B1 * | 6/2002 | Foltzer | | 385/7 |
| 7,113,660 B2 * | 9/2006 | Andrews et al. | | 385/13 |
| 7,212,696 B2 * | 5/2007 | Andrews et al. | | 385/13 |
| 7,245,789 B2 * | 7/2007 | Bates et al. | | 385/7 |
| 7,397,596 B2 * | 7/2008 | Yacoubian | | 359/290 |
| 7,447,388 B2 * | 11/2008 | Bates et al. | | 385/7 |
| 7,660,492 B2 * | 2/2010 | Bates et al. | | 385/7 |
| 7,966,883 B2 * | 6/2011 | Lorraine et al. | | 73/601 |
| 8,059,923 B2 * | 11/2011 | Bates et al. | | 385/7 |
| 8,290,316 B2 * | 10/2012 | Molin et al. | | 385/12 |
| 8,391,652 B2 * | 3/2013 | Bates et al. | | 385/7 |

* cited by examiner

*Primary Examiner* — J M Saint Surin
(74) *Attorney, Agent, or Firm* — Lawrence S. Cohen

(57) ABSTRACT

An apparatus and method for testing composite structures in which ultrasonic waves are used to detect disbonds in the structures are described. The apparatus comprises a flexible structure carrying acousto-optical transducers such as fiber Bragg gratings. During use, the apparatus is mechanically and conformally coupled to the structure under test.

22 Claims, 8 Drawing Sheets

APPARATUS AND METHOD FOR DAMAGE LOCATION AND IDENTIFICATION IN STRUCTURES

CROSS REFERENCE TO RELATED APPLICATIONS

The present application is a continuation of application Ser. No. 12/504,595 filed on Jul. 16, 2009 now U.S. Pat. No. 8,234,924 which claims priority to U.S. Provisional Application 61/081,706 filed on Jul. 17, 2008, both of which are incorporated herein by reference in their entirety.

STATEMENT OF GOVERNMENT GRANT

This invention was made with Government support under contract numbers FA8501-06-M-0106 and FA8501-07-C-0025 from the U.S. Air Force. The Government may have certain rights in this patent.

FIELD

The present disclosure relates to an apparatus and method for damage location and identification in structures. More in particular, it relates to an apparatus and method for noninvasive detecting and locating of defects in composite structures using ultrasonic waves.

BACKGROUND

Measurement of ultrasonic vibrations by means of fiber Bragg gratings (FBGs) that are embedded into the component under test or glued to the component surface are discussed, for example, in "Acousto-ultrasonic sensing using fiber Bragg gratings", Daniel C Betz et al, 2003 Smart Mater. Struct. 12 122-128 or "Impact wave and damage detections using a strain-free fiber Bragg grating ultrasonic receiver", Jung-Ryul Lee et al, NDT & E International Volume 40, Issue 1, January 2007, 85-93.

SUMMARY

According to a first aspect of the present disclosure, a method for nondestructive testing of structures is provided, comprising: causing an ultrasonic wave to traverse a portion of a structure being tested for presence of defects, to cause surface displacements in the structure; providing one or more optical waveguides attached to a flexible structure, each optical waveguide comprising one or more spaced apart transducers adapted to respond to the surface displacements; locating the one or more transducers in mechanical contact with the surface of the structure under test for a transducer response corresponding to the surface displacements of the structure at respective locations of the transducers caused by the ultrasonic wave; obtaining modulation of the one or more transducers in response to the surface displacements of the structure; based on the response of the one or more transducers, reconstructing distribution characteristics of the ultrasonic waves across the structure; and based on the reconstructed distribution characteristics, determining likely locations of features in the structure, such as damages.

According to a second aspect of the present disclosure, a nondestructive evaluation apparatus for use in responding to surface displacements caused by ultrasonic waves on a surface of a material or structure under test is provided, the apparatus comprising: a flexible structure having attached thereto one or more optical waveguides, each optical waveguide comprising at least one acoustic-optical transducer, wherein the flexible structure is adapted to follow the surface displacements in strain and/or bending such that modulation of the at least one acoustic-optical transducer is communicated through the optical waveguide to enable processing to determine information on the surface displacement.

According to a third aspect of the present disclosure, an apparatus for determining locations of delaminations and/or disbonds in a composite piece part is provided, comprising: an acoustic source for generating, during operation of the apparatus, ultrasonic waves in the composite piece part; and a compliant planar member connected with the acoustic source and adapted for conforming to at least a portion of the composite piece part, the compliant planar member comprising one or more optical waveguide tracks located on a surface thereof, the one or more optical waveguide tracks comprising at least one FBG acoustically coupled to the acoustic source, the at least one FBG acting, during operation of the apparatus, as an acousto-optical transducer of acoustic signals generated by the acoustic source, the at least one FBG located at a predetermined distance from the acoustic source.

According to a fourth aspect, an apparatus comprising a dimensionally stable, conformable member having a first and at least one second location separated by a known distance is provided, wherein a source of ultrasonic energy is located at the first location and at least one acousto-optical transducer is located at the at least one second location, the source being adapted to be acoustically coupled to the at least one optical transducer by placement of the conformable member on a device under test.

According to a fifth aspect, a method to determine dynamic strain and/or bending of one or more optical filters is provided, comprising: performing a first sweeping of a tunable laser to acquire reflection spectra of the one or more optical filters; for each optical filter, determining a feature of the reflection spectrum of that optical filter; and performing a second sweeping of the tunable laser to acquire acousto-ultrasound responses of the one or more optical filters.

Further aspects of the present disclosure are provided in the specification, drawings and claims of the present application.

DETAILED DESCRIPTION

The structure to be imaged through ultrasonic inspection in accordance with the teachings of the present disclosure can be any structure capable of transmitting ultrasound from the source to the receiving elements. By way of example, such structure can include simple single plate-like structures including either metals or polymers or composites, where polymers include resins. By way of further example, the structure can include compound plate-like structures that are multiple layers of either metals or composites or both. The second layer that the composite is adhered to can be a metal honeycomb or a polymer, e.g. a Nomex® honeycomb.

Figure 1:
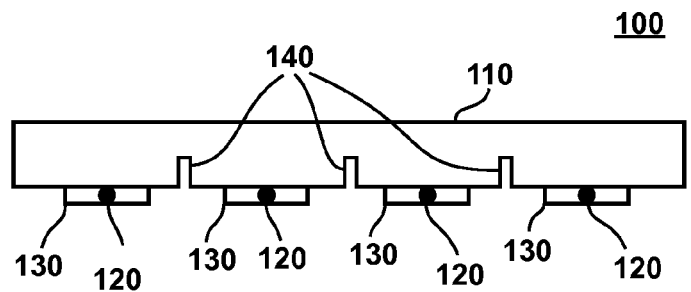
FIG. 1 shows a cross-sectional view of an embodiment of a flexible sheet or panel comprising a plurality of FBGs according to the disclosure.

FIG. 1 shows a cross-sectional view of an embodiment of a flexible sheet or panel comprising a plurality of FBGs according to the disclosure. In particular, the embodiment of FIG. 1 shows an ultrasound imaging device (100) comprising a flexible sheet or panel (110) to which a plurality of FBGs (120), possibly enclosed by coatings or encasings (130), is connected.

The FBGs (120) are adapted to be acoustically coupled, e.g. through friction, to a surface on an object under test, not shown in the figure. In order to strengthen the mechanical contact between the FBGs and the surface of the object under test, a plurality of suction pockets (140) can be provided. Once the suction pockets (140) are actuated (e.g., through suction hoses not shown in the figure), the mechanical contact between the flexible sheet or panel (110) and the surface of the object under test is increased due to ambient air pressure.

The functions of flexible sheet or panel (110) are (i) conformability to the shape of the component under test, (ii) to be dimensionally stable, i.e. to provide a predetermined lateral position of the transducers with respect to the acoustic source and to each other, if more than one, and (iii) provide sufficient mechanical pressure to each of the transducers such that acoustic coupling between transducer and surface is provided.

Flexible sheet or panel (110) has sufficient flexibility to conform to the shape of the component under test and to allow for the FBGs to be compressed, stretched, and/or bent by the ultrasonic surface deformations of the component under test and to hold the FBGs in place by exerting a force on them as they are acoustically coupled to the component. This flexibility allows the sheet or panel to conform to non-planar surfaces of such component.

By way of example, the flexible sheet or panel can be a flexible sheet or panel made of metal, polymer, or rubber of uniform or non-uniform thickness, such as tapered or ribbed, for instance, with a regular or irregular pattern and/or embossing. The surface of the sheet or panel should provide substantially uniform pressure over the area of any single transducer to permit good acoustic contact at the transducer. The flexibility of the sheet or panel can be such that it allows bending to the extent that the embedded fiber is not prone to breakage when the sheet or panel is bent.

The flexible sheet or panel is able to conform to the surface shape such that the transducers are in good acoustic contact. Therefore, different hardness polymers can be used, depending on the potential curvature of the surface under test. According to an embodiment of the disclosure, the flexible sheet or panel is a poor acoustic waveguide itself, in order not to influence the measurement of the material under test. A flexible sheet or panel according to such embodiment could be, for example, a flexible sheet or panel made of rubber.

As mentioned above, the mechanical contact between the FBGs and the surface of the structure under test can be strengthened through mechanical means such as underpressure between the sheet or panel (110) and the surface, causing ambient air to press the sheet or panel against the surface.

Figure 2:
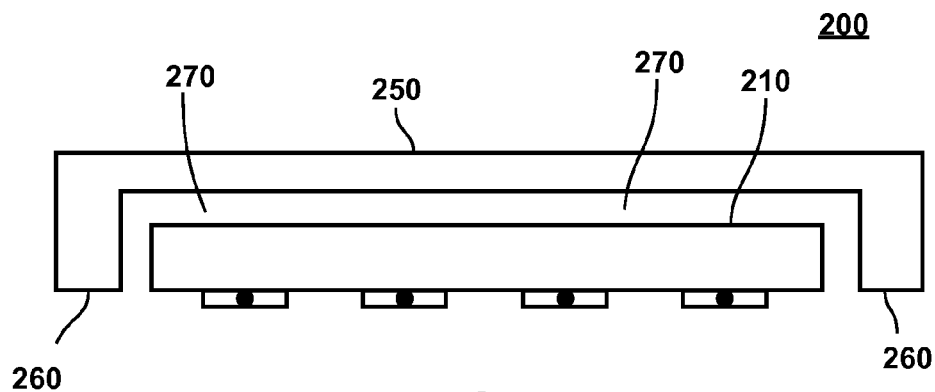
FIG. 2 shows a cross-sectional view of another embodiment of the flexible sheet or panel, where a suction cup is also provided.

An alternative mechanical means to increase such contact is shown in the embodiment of FIG. 2.

FIG. 2 shows a cross-sectional view of another embodiment of the flexible sheet or panel, where a suction cup is also provided. In particular, the embodiment of FIG. 2 shows an ultrasound imaging device (200) comprising a flexible sheet or panel (210) similar to the embodiment of FIG. 1 coupled with a suction cup (250), e.g. a polyurethane suction cup. During operation of the ultrasound imaging device (200), underpressure (i.e. formation of vacuum) in the region (270) is obtained, thus providing a stronger contact between sheet or panel (210) and the surface of the device under test. If desired, compressible foam can be located in the region (270) between flexible sheet or panel (210) and suction cup (250). The embodiment of FIG. 2 will also be later discussed, with reference to the depiction of FIG. 6.

Figure 11:
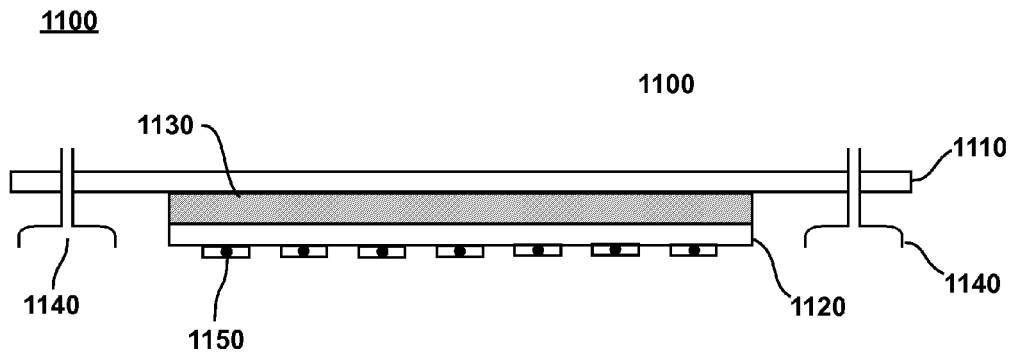
FIG. 11 shows a cross-sectional view of a further embodiment of the flexible sheet or panel, where suction cups located on the side of the sheet or panel are provided.

The embodiment of FIG. 2 shows an evacuation technique were the entire lid (250) gets evacuated. Alternative embodiments are possible where, for example, suction cups are attached to a side of the lid, which is rigid, and pushes down on sheet or panel (210) when underpressure is formed. Reference can be made, for example, to the embodiment of FIG. 11, where a rigid pressure plate or lid (1110) is located on top of a compressible sheet (1120) (e.g., a compressible soft polymer sheet), with a layer (1130) of compressible foam located between the two. Also shown in FIG. 11 are vacuum suction cups (1140) (e.g., polyurethane cups) on the sides of the structure.

Increasing the acoustic contact between the optical transducers that are embedded in a flexible backing and the surface of the structure under test can also be achieved by applying mechanical force directly instead of a suction-induced force. This can be obtained through the use of hydraulic pressure or by the use of known weights.

Figure 12:
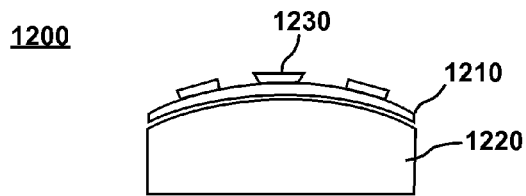
FIGS. 12 and 13 show cross-sectional views of further embodiments of the flexible sheet or panel, where magnetic holders are provided.
Figure 13:
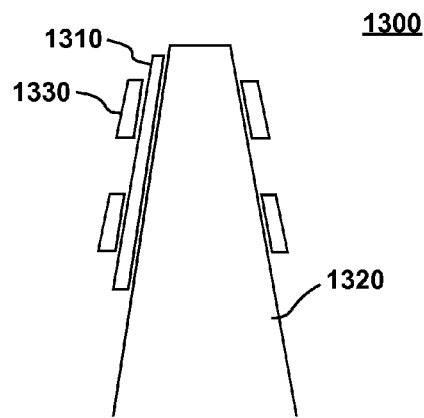

For the structures under test whose acousto-ultrasonic characteristics are measured and that are made of materials containing iron, cobalt or nickel, a magnet can be provided to apply pressure to the flexible sheet or panel of transducers, as shown in FIG. 12, where a flexible sheet or panel (1210) located on a structure or device under test (1220) and three magnetic holders (1230) are depicted. Non-magnetic structures like, for example, structure (1320) of FIG. 13, can have two magnets (1330) on either side of the structure (1320) to hold the flexible sheet or panel (1310) on one side or both sides of the structure (1320).

Figure 14:
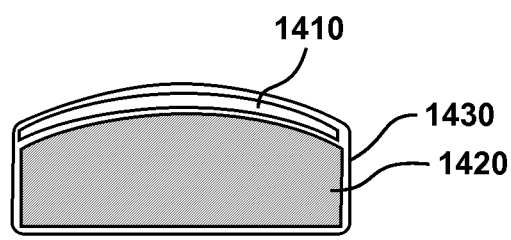
FIGS. 14 and 15 show cross-sectional views of further embodiments of the flexible sheet or panel, where an external cover is provided.
Figure 15:
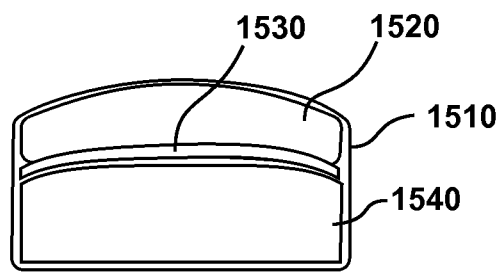

Another method can be the use of a mechanical "pull" from a part that has some elastic or tensioning capability that goes (at least partly) around the flexible sheet or panel contacting the structure under test, as in FIG. 14, where a flexible sheet or panel (1410) located on a structure or device under test (1420) are shown, and where both the sheet and the structure are embedded into a cover or sock (1430). By way of example, a strap around the vertical stabilizer wing could produce pressure onto the panel by being pulled tight or by being partly elastic. Additionally, also a more loose fitting rigid non-elastic strap or "sock" (1510) can be provided, in which an inflatable element (1520) is interspersed between such sock (1510) and the flexible sheet or panel (1530) to provide the pressure between panel (1530) and surface (1540) when inflated, as shown in FIG. 15.

Therefore, upon reading of the above explained embodiments of FIG. 1 and FIG. 2, the person skilled in the art will understand that a flexible sheet or panel containing the FBGs can conveniently be temporarily attached and removed from the component surface, and thus can be used for rapid subsequent measurements of multiple sections on a larger surface or for testing multiple components with the same FBG transducers.

The sheet or panel has sufficient flexibility to allow for the FBGs to be compressed, stretched, and/or bent by the ultrasonic surface deformations of the component under test. Flexibility of the sheet or panel makes it possible to test parts with complex shapes, such as encountered in aircraft components and multiple other applications. The sheet or panel is lightweight and convenient to handle and attach.

Figure 3:
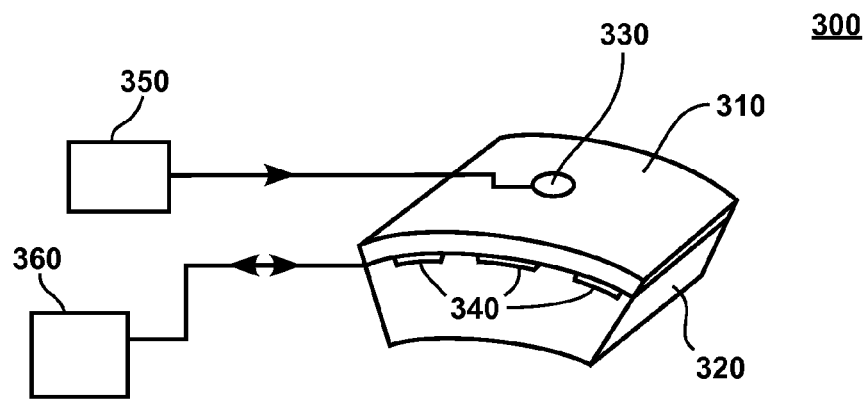
FIG. 3 shows a schematic perspective view of an arrangement, where a flexible sheet or panel is coupled to a composite structure.

FIG. 3 shows a schematic perspective view of an arrangement (300), where a flexible sheet or panel (310) is coupled to a composite structure (320). By way of example, a surface wave, also called Lamb wave, is generated along the composite structure (320) through an ultrasonic source (330), such as a piezoelectric (PZT) transducer. The surface wave thus generated is detected by the FBGs (340). Ultrasonic source (330) can be powered by ultrasonic generator (350), while the FBG powering/control and readout circuitry, including a processor, is generally indicated with (360) and will be later shown in detail with reference to the embodiment of FIG. 9.

Figure 4:
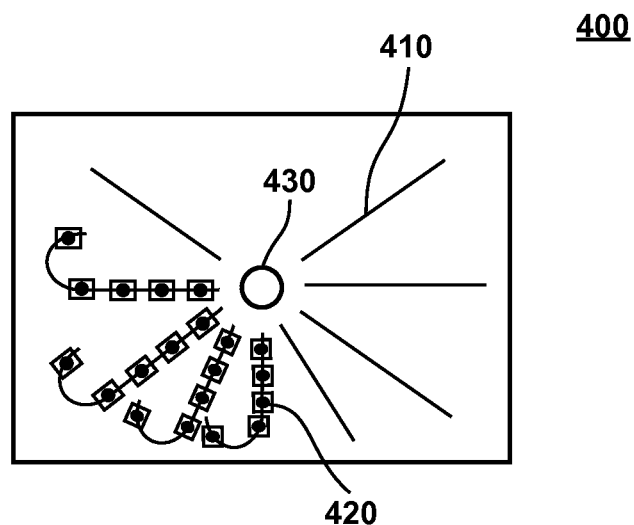
FIG. 4 shows a bottom view of the flexible sheet or panel of the present disclosure where a first example of disposition of the FBGs is shown.

FIG. 4 shows a bottom view of the flexible sheet or panel of the present disclosure where a first example of disposition of the FBGs is shown. In particular, the embodiment of FIG. 4 shows, as seen from a bottom or contact surface, a flexible sheet or panel (400) having attached a plurality of optical fiber tracks (410), on which FBGs (420) are located. Some of the optical fibers (410) have a curved shape, so that additional FBGs (420) can be located on the same optical fiber. Also shown in FIG. 3 is a PZT source (430).

Figure 5:
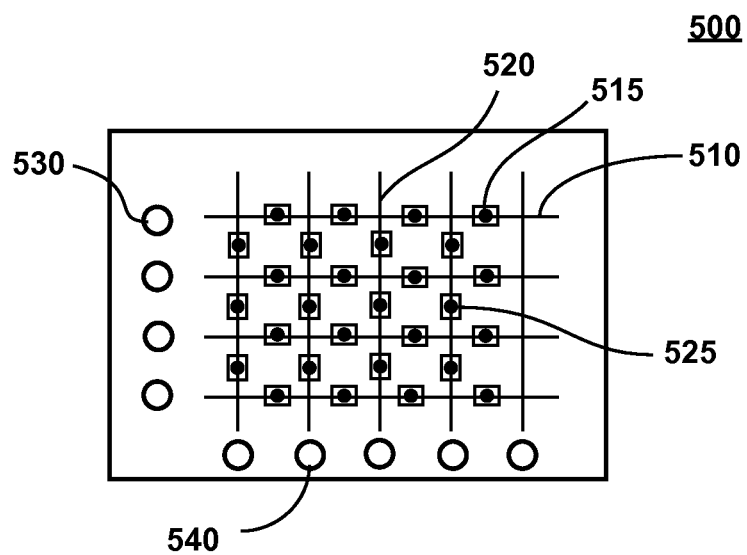
FIG. 5 shows a bottom view of the flexible sheet or panel of the present disclosure where a second example of disposition of the FBGs is shown.

FIG. 5 shows a bottom view of the flexible sheet or panel of the present disclosure where a second example of disposition of the FBGs is shown. In particular, the embodiment of FIG. 5 shows, as seen from a bottom or contact surface, a flexible sheet or panel (500) having attached a plurality of horizontal optical fiber paths or tracks (510) and a plurality of vertical optical fiber paths or tracks (520) in a matrix configuration. The FBGs can be located (515) on the horizontal tracks (510) and/or be located (525) on the vertical tracks (520). Also shown in the figure are a first plurality of PZT sources (530) and a second plurality of PZT sources (540).

Figure 6:
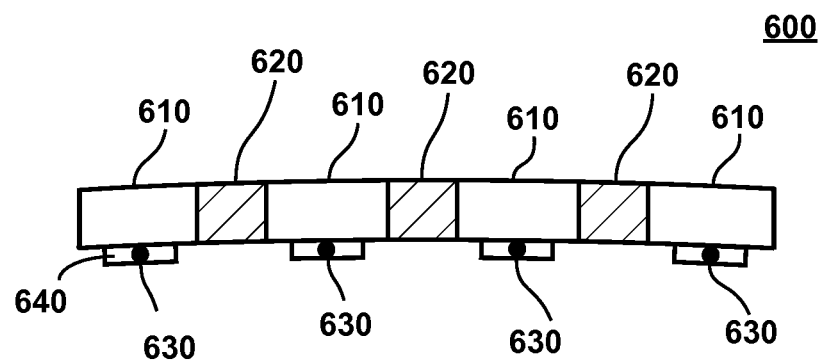
FIG. 6 shows a cross-sectional view of a further arrangement of the flexible sheet or panel.

The embodiments of FIG. 5 and FIG. 6 show two examples of spaced apart FBGs acting as ultrasonic receivers. The FBGs are spaced apart at known distances from the acoustic source (e.g., the PZT source) along their respective optical fibers. Each FBG along a fiber corresponds to a different Bragg wavelength, so that the reflected signal can be associated with a specific FBG. The FBGs detect the wave by strain and/or bending and the amount of the measured strain and/or bending is correlated with the wave amplitude. Then the location of any such strain and/or bending can be determined by processing the matrix of properties such as a wave amplitude and/or time of arrival. In particular, the use of a flexible sheet or panel having a plurality of optical fibers with spaced apart FBGs provides multiple ultrasonic measurements on the structure under test at pre-determined locations as sensed by the FBGs.

Therefore, by using a plurality of sensing locations in a matrix or non-matrix configuration, the wave amplitude can be determined at a plurality of points and then the location of strain and/or bending can be determined through an algorithm that processes the FBG locations and the measured wave properties. In this way, the distribution of ultrasonic waves across the component surface is reconstructed, and information about the structural integrity of the component is gained.

FIG. 6 shows a cross-sectional view of a further arrangement of the compliant member (e.g., a net) or flexible sheet/ panel. In particular, the embodiment of FIG. 6 shows an ultrasound imaging device (600) comprising rigid sections (610) interleaved with flexible sections (620). In the embodiment of FIG. 6, the FBGs (630) are located in correspondence of the rigid sections (610). Therefore, in the embodiment of FIG. 6 flexibility of the device (600) is obtained through the presence of the flexible sections or regions (620).

Figure 7:
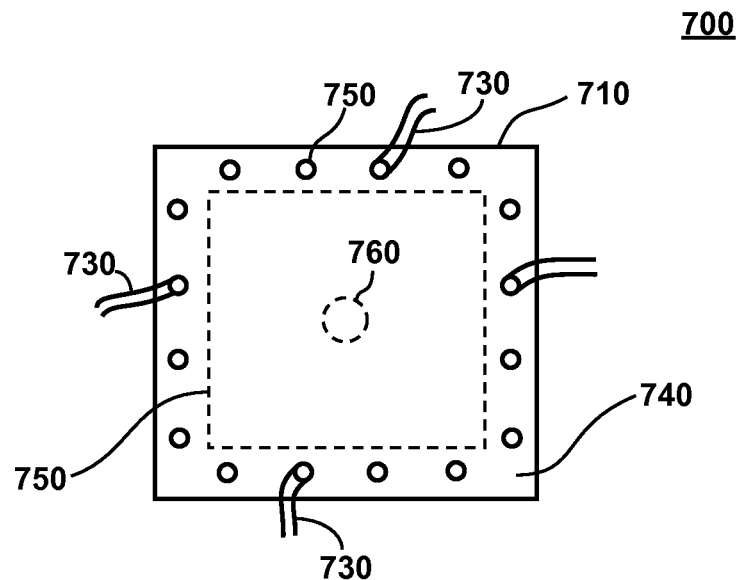
FIG. 7 shows a top view of the flexible sheet or panel.

FIG. 7 shows a top view of the flexible sheet or panel. In particular, the embodiment of FIG. 7 corresponds to the embodiment of FIG. 2 and shows a plan view of suction cup (710) which comprises a plurality of holes (720) with inserted suction hoses (730) to create underpressure in a region (740) between top suction cup (710) and bottom flexible sheet or panel (750). Also shown in FIG. 7 is a PZT source (760) located in the flexible sheet or panel (750).

Figure 8:
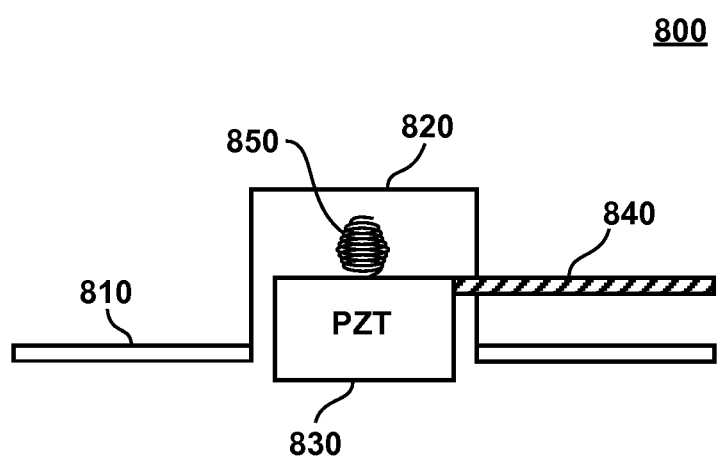
FIG. 8 shows a cross-sectional view of a PZT source to be used in accordance with the teachings of the present disclosure.

Location of PZT sources on ultrasound imaging devices is known per se to the person skilled in the art and will not be discussed here in detail. FIG. 8 shows a way devised by applicants to integrate a PZT source on the top surface of the suction cup previously discussed in FIG. 7. More in particular, FIG. 8 shows a cross-sectional view of an arrangement (800), where a pressure plate (810), such as suction cup (710) of FIG. 7, is provided with an aluminum casing (820) containing a PZT source (830) powered by an acoustic generator (not shown) through a cable (840) and held in place into the casing by a spring (850) or any elastic material.

Figure 9:
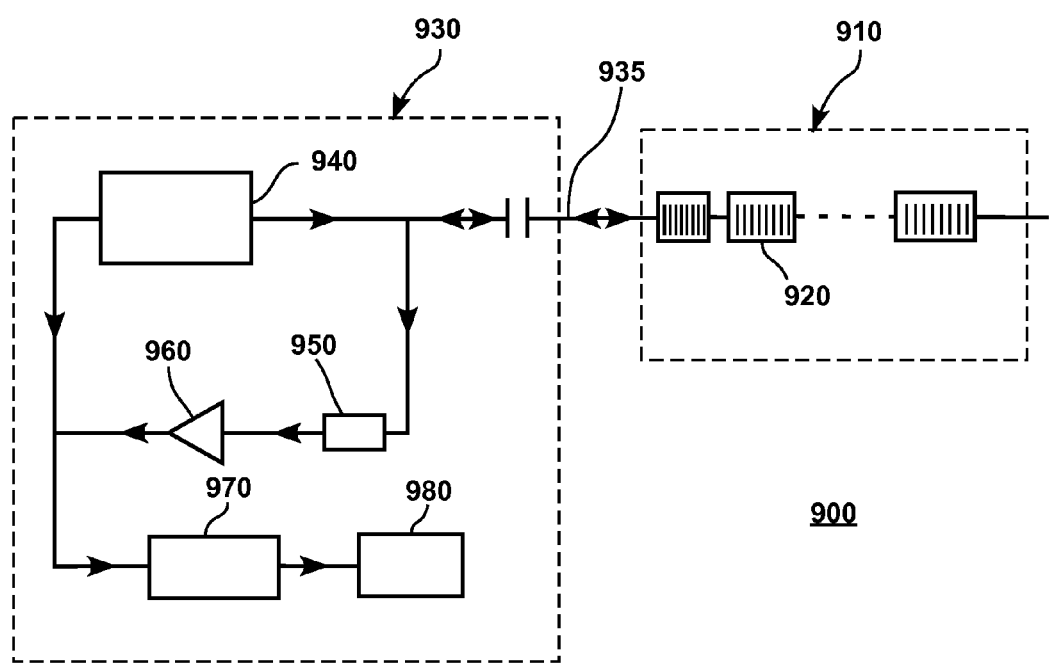
FIG. 9 shows an example of a control arrangement of the flexible sheet or panel.

FIG. 9 shows an example of a control arrangement of the flexible sheet or panel. In particular, the schematic diagram of FIG. 9 shows an arrangement (900) comprising a flexible sheet or panel (910)—which includes a plurality of FBGs (920)—and a control system (930). While this system shows the reflected signal from the FBGs going to the photodetector, a signal transmitted by the FBGs can alternatively be used by optically coupling the fiber end to the photodetector. The flexible sheet or panel (910) and the control and/or processing system (930) are optically connected (935). The control system (930) comprises a tunable laser (940), a photodetector (950), feedback circuitry (960), a data acquisition and signal processing module (970), and a display (980).

In operation, the tunable laser (940) optically powers the FBGs (920), while the photodetector (950) receives, in reflection (or transmission), the modulated outputs of the FBGs (920) and sends them to the signal processing module or processor (970), which analyzes the data and displays them on display (980). In particular, the resulting modulation in reflection wavelength on each FBG (920) is used for reconstructing the distribution of ultrasonic waves across the component surface, and consequently for gaining information about the structural integrity of the component.

If desired, the readout circuitry can also include one or more additional PZT transducers, located at a distance from the PZT transducer acting as an ultrasonic source, e.g. 6 cm, for sensing waves at defined points. By way of example, each PZT transducer can operate at frequencies up to 1.5 MHz, and the source signal can be a single cycle sine pulse with a center frequency of 250 kHz and 10 Volts.

Figure 10:
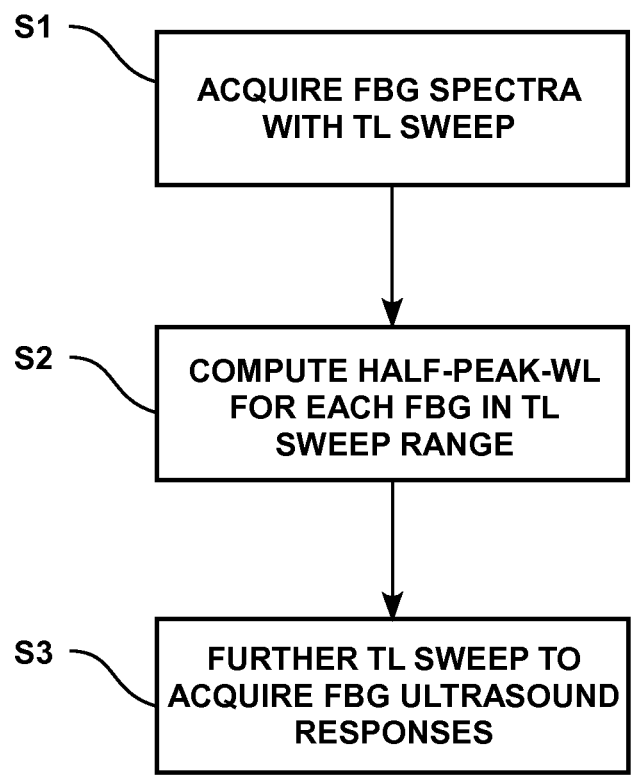
FIG. 10 shows a flow chart of a tunable laser sweeping technique in accordance with the disclosure.

In the following paragraphs, a dynamic strain readout process or method in accordance with an embodiment of the present disclosure will be described. The process described below performs readout while compensating for static effects at the FBG locations. Reference will be made to FIG. 10.

In a first step S1, FBG spectra are acquired by sweeping a tunable laser (TL), see, e.g., laser (940) of FIG. 9. More in particular, a wavelength swept tunable laser is scanned/swept while incident on a fiber with one or many FBGs, see, e.g., elements (910) and (920) of FIG. 9. The reflected/transmitted intensity as a function of time is obtained. When the time scale is calibrated to wavelength, this intensity variation represents the (one or many) FBG spectra.

In a second step S2, one or both of the two wavelengths at half-peak intensity of the FBG reflection spectrum (half-peak-WL) are determined for each FBG in the entire TL sweep range and stored. For example, the peak intensity of the FBG spectra is determined and one or both of the half maxima (for reflection) or minima (for transmission) intensity are determined, called the "half-peak-WL". These values are computed from the spectra and stored for all the FBGs that are "read" in a single sweep/scan made by the TL. The person skilled in the art will also understand that other wavelengths can be acceptable, such as wavelengths within a quarter linewidth distance from the half-peak-WL, where a linewidth is defined as full width half maximum (FWHM) of the reflected spectrum.

In a third step S3, a further sweep of the TL is performed (e.g., within minutes of reading the FBG spectra and storing the half-peak-WLs as above), during which the following sub-steps are performed: (a) stop at the first FBG's stored half-peak-WL for a sufficient time to acquire an acousto-ultrasound response at this FBG location; (b) go to the next FBG's half-peak-WL and repeat acousto-ultrasound response acquisition; and (c) repeat until all FBG's ultrasound responses are acquired. Therefore, this additional sweep is not a continuous sweep, because it stops at the previously stored half-peak-WLs of each FBG.

It should be noted that the time difference between storing of the half-peak-WL's in the second step and acquisition of the acousto-ultrasonic responses in the third step is a time period during which significant temperature changes are not expected to occur, for instance less than a few minutes.

In the case where several optical fiber strands having (one or many) identical FBGs of identical spectra are used, an optical switch can be provided, to re-direct each TL sweep to each individual fiber strand and repeat the double sweeping process above to acquire acousto-ultrasonic response at all FBG locations.

The timing of the above described readout process will now be discussed. In general, the readout of the acousto-ultrasonic response is commenced after mounting of the acousto-ultrasonic imaging system on the device under test. During the process of placing the flexible sheet or panel comprising the transducers on the device under test the transducer or transducers could be subject to bending to conform to the curvature of the structure. In addition, the transducers could also undergo a change in temperature if the initial temperatures of the sheet and the device under test are different. Appropriate waiting time should be allowed for the temperature stabilization of the imaging device with the flexible sheet or panel. When the bending and the temperature changes have stabilized such that no significant static changes in these are to be deliberately performed or foreseen, the above readout process that compensates for all static changes that have occurred prior to this time, is commenced.

An embodiment of the above two-step sweeping process has been described with reference to FBGs. However, in addition to FBGs there are various other ways that a narrow-band optical filter can be realized in optical waveguides that may yield a filtering action in reflection or transmission. These include Fabry-Perot cavities that are formed extrinsically at the end of the waveguide (and operated in reflection mode) or intrinsically in the middle of the waveguide. A Fabry-Perot cavity can be realized by having two parallel reflectors of variable reflectivity separated by an optical medium that is not opaque. The two reflectors may also be formed by two FBGs instead of two reflecting surfaces. The transmission or reflection spectrum of this device is then characterized by changes in the reflectivity and changes in the refractive index or the separation of the cavity thus formed, which thus responds to bends or axial stretches along an optical waveguide axis. Dynamic strain events, such as acousto-ultrasound, can be measured by the same two-step process described above.

By way of the above described embodiment, one or many locations of dynamic strain response can be measured in an automated fashion thus compensating for slowly changing static strain and/or temperature changes. Such changes would otherwise prevent the acquisition of a maximum dynamic strain response (off from the Quadrature-point) by causing a relative shift between the tunable laser and FBG spectra.

Optical filters such as fiber Bragg grating filters and Fabry-Perot cavities have been described above with reference to optical fiber waveguides. However, those versed in the art will understand that the teachings of the present disclosure can also apply, more generally, to optical waveguides not limited to optical fiber waveguides, such as rectangular waveguides.

The teachings of the present disclosure provide simple and effective tools in detecting damage in composite and/or metallic structures. The damage could be, for example, a disbond or delamination between the layers below the superficial layer at which the ultrasound is launched into the object under test. The term "delamination" is defined to mean a localized failure of the bond between the composite layers of a composite structure. The term "disbond" is defined to mean a localized failure of the bond between a composite layer stack and the underlying structure, e.g. an aluminum honey-comb core. Such teachings can be used to develop structural health monitoring systems for aging as well as new aerospace and aircraft structures, resulting in significant reductions in the life cycle cost of these structures.

The examples set forth above are provided to give those of ordinary skill in the art a complete disclosure and description of how to make and use the embodiments of the apparatus and method for damage location and identification in structures of the disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods, apparatus or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A nondestructive evaluation apparatus for use in responding to surface displacements caused by ultrasonic waves on a surface of a material or structure under test, the apparatus comprising:
a dimensionally stable conformable flexible sheet or pad or panel having attached thereto a plurality of optical waveguides, each optical waveguide comprising a plurality of spaced apart acousto-optical transducers adapted to be placed in mechanical contact with the surface under test and to respond to surface displacements of the surface of the structure under test caused by ultrasonic wave energy in the structure by modulation of the wavelength of optical energy transiting the transducer and is communicated through the waveguides to enable processing of the optical modulation of each transducer;
one or more ultrasonic wave sources adapted to inject ultrasonic vibration into the structure and thereby on the surface on which the transducers are positioned;
the transducers being located on the sheet or pad in known spatial relationship to each other and to the one or more ultrasonic wave sources;
means for receiving from the waveguides and processing the optical modulation of the transducers caused by the ultrasonic vibration of the surface for reconstruction of the distribution of ultrasonic wave variations across the surface and determining therefrom information about structural characteristics of the structure under test and providing such information to users.

2. The nondestructive evaluation apparatus of claim 1, wherein the transducers are FBGs that respond in bending and/or strain to measure the surface displacement of the structure under test caused by the ultrasonic wave.

3. The nondestructive evaluation apparatus of claim 1, further comprising one or more magnets located on the apparatus when coupled to the material or structure under test thereby to mechanically couple the transducers to the surface.

4. The nondestructive evaluation apparatus of claim 1, wherein the one or more ultrasonic wave source(s) is/are a piezoelectric (PZT) transducer.

5. The nondestructive evaluation apparatus of claim 1, further comprising a readout circuitry to process optical signals output by the acousto-optical transducers.

6. The nondestructive evaluation apparatus of claim 1 wherein the transducers are FBGs adapted to respond in strain and/or bending to the surface displacement of the structure under test.

7. The nondestructive evaluation apparatus of claim 6 wherein the FBGs at least of each optical waveguide has a different Bragg wavelength.

8. The nondestructive evaluation apparatus of claim 1 wherein all of the FBGs are spaced apart at known distances from the acoustic source and from each other.

9. The nondestructive evaluation apparatus of claim 8 wherein the optical waveguides are attached to the conformable flexible sheet or pad in a selected array formation so as to place the FBGs at identified spaced apart positions relative to the array formation to define a matrix of the transducers.

10. An apparatus for determining locations of delaminations and/or disbonds in a composite piece part, comprising:
an acoustic source for generating, during operation of the apparatus, ultrasonic waves in the composite piece part thereby causing ultrasonic vibration of a surface of the composite piece part; and
a compliant planar member configured for conforming to at least a portion of the composite piece part surface, the compliant planar member comprising one or more optical waveguide tracks located on a surface thereof, the one or more optical waveguide tracks comprising at least one FBG coupled to the composite piece part surface, the at least one FBG acting, during operation of the apparatus, as an acousto-optical transducer of signals generated by the acoustic source by the resultant vibrations of the composite piece part surface, the at least one FBG located at a predetermined distance from the acoustic source.

11. The apparatus of claim 10, wherein the acoustic source is a PZT transducer.

12. The apparatus of claim 10, wherein the compliant planar member is chosen from a flexible sheet, a panel, or a net.

13. The apparatus of claim 12, wherein the flexible sheet, panel or net is a flexible polymer sheet, panel or net.

14. The apparatus of claim 10, wherein the at least one FBG are a plurality of FBGs, each corresponding to a different Bragg wavelength.

15. The apparatus of claim 10, wherein the one or more optical waveguide tracks are coupled to a processor, the processor being operative to reconstruct distribution characteristics of the ultrasonic waves as transduced by response to the surface vibration caused by the ultrasonic waves and reflected by the at least one FBG.

16. The apparatus of claim 10, wherein the compliant planar member comprises rigid sections interleaved with flexible sections.

17. The apparatus of claim 16, wherein the at least one FBG is located in correspondence of the rigid sections.

18. A system operative for determining structural condition of a structure (a subject body) under test having a surface and being capable of transmitting ultrasound comprising:
a subject body under test for purposes of determining the structural integrity or variations in the structure of the subject body and having a surface and being capable of receiving and transmitting in it ultrasonic energy to cause ultrasonic vibration of the surface defined as surface displacements;
a dimensionally stable conformable flexible sheet or pad or panel (collectively a conformable member) applied to a selected area of the surface which is to be under test;
at least one acoustic source for generating an ultrasonic wave or waves in the structure under test, to cause surface displacements;
a plurality of optical waveguides attached to the conformable member, each optical waveguide comprising a plurality of spaced apart transducers of the type that will modulate an optical signal sent from a control system through the waveguide and transiting the transducer from the sensing of ultrasonic mechanical vibration, which are responsive by modulation of a transiting optical signal to surface displacements of the surface under test when in mechanical contact with the surface and transmitting the modulated optical signal in the waveguide to the control system and each of said transducers being located at specific locations on the conformable member having a predetermined location with respect to the at least one acoustic sources and to each other;

means to provide sufficient mechanical pressure to the transducers to be employed in a test such that mechanical coupling between the transducer and the surface under test is provided to obtain transducer response to surface displacement of the structure at the respective locations of the transducers caused by the acoustic wave or waves generated in the subject body by the at least one acoustic source;

a control system connected to the plurality of optical waveguides for generating optical signals into the waveguides and the transducers and for receiving optical signals that have been reflected by or passed through the transducers and determining optical modulation by the transducers in response to the surface displacements of the structure and for reconstructing distribution characteristics of the ultrasonic waves across the structure under test and based on the reconstructed distribution characteristics determining likely locations of features in the structure.

19. The system of claim 18 the transducers comprising FBGs adapted to respond in strain and/or bending to the surface displacement of the structure under test.

20. The system of claim 19 wherein the FBGs at least of each optical waveguide has a different Bragg wavelength.

21. The system of claim 19 the optical waveguides being attached to the conformable member in a selected array formation whereby the transducers are located at identified spaced apart positions relative to the array formation to define a matrix of the transducers on the surface.

22. The system of claim 18 wherein the means to provide mechanical pressure to couple the transducers to the structure under test comprises suction pockets distributed in the conformable member.

* * * * *